United States Patent
Yoshioka et al.

(10) Patent No.: US 12,037,708 B2
(45) Date of Patent: *Jul. 16, 2024

(54) METHOD FOR PRODUCING THREAD BUNDLE OF BAGWORM SILK THREAD

(71) Applicants: NATIONAL AGRICULTURE AND FOOD RESEARCH ORGANIZATION, Ibaraki (JP); KOWA COMPANY, LTD., Aichi (JP)

(72) Inventors: Taiyo Yoshioka, Ibaraki (JP); Tsunenori Kameda, Ibaraki (JP); Akimune Asanuma, Ibaraki (JP); Keitaro Hattori, Ibaraki (JP); Norihiko Fukuoka, Ibaraki (JP)

(73) Assignees: NATIONAL AGRICULTURE AND FOOD RESEARCH ORGANIZATION, Ibaraki (JP); KOWA COMPANY, LTD., Aichi (JP)

( * ) Notice: Subject to any disclaimer, the term of this patent is extended or adjusted under 35 U.S.C. 154(b) by 891 days.

This patent is subject to a terminal disclaimer.

(21) Appl. No.: 17/046,467

(22) PCT Filed: Apr. 16, 2019

(86) PCT No.: PCT/JP2019/016308
§ 371 (c)(1),
(2) Date: Nov. 10, 2020

(87) PCT Pub. No.: WO2019/203228
PCT Pub. Date: Oct. 24, 2019

(65) Prior Publication Data
US 2021/0161115 A1    Jun. 3, 2021

(30) Foreign Application Priority Data
Apr. 16, 2018   (JP) .................. 2018-078522

(51) Int. Cl.
*D01B 7/00*    (2006.01)
*A01K 67/04*    (2006.01)
*D01C 3/02*    (2006.01)

(52) U.S. Cl.
CPC ............... *D01B 7/00* (2013.01); *A01K 67/04* (2013.01); *D01C 3/02* (2013.01)

(58) Field of Classification Search
CPC ................... D01B 7/00; D01C 3/02
See application file for complete search history.

(56) References Cited

U.S. PATENT DOCUMENTS

| | | | |
|---|---|---|---|
| 2006/0147401 A1* | 7/2006 | Tanaka | A61Q 19/08 424/70.13 |
| 2021/0172089 A1* | 6/2021 | Yoshioka | D01F 4/00 |
| 2021/0372007 A1* | 12/2021 | Yoshioka | D01F 4/00 |

FOREIGN PATENT DOCUMENTS

| | | |
|---|---|---|
| EP | 3733937 A1 | 11/2020 |
| JP | 2001207325 A | 8/2001 |

(Continued)

OTHER PUBLICATIONS

Osaki, "Animals Teach Science on Natural Fibers: Spider's Silks, Bagworm's Silks, Collagen Fibers", Journal of the Society of Fiber Science and Technology, 2002, vol. 58, No. 3, 5 pages, English translation 3 pages.

(Continued)

*Primary Examiner* — Shaun R Hurley
(74) *Attorney, Agent, or Firm* — Lucas & Mercanti, LLP

(57) ABSTRACT

Provided is a method developed for producing a thread bundle with high efficiency in terms of spun thread collection and without causing mechanical damage to a foothold silk thread spun by a bagworm onto a base material. After a bagworm is placed along with a solvent-soluble base material and allowed to spin the foothold silk thread onto the (Continued)

surface of the base material, the base material is dissolved with a solvent to separate the foothold silk thread therefrom.

11 Claims, 4 Drawing Sheets

(56) References Cited

FOREIGN PATENT DOCUMENTS

| | | |
|---|---|---|
| JP | 2001207585 A | 8/2001 |
| WO | 2012165477 A1 | 12/2012 |
| WO | 2013065651 A1 | 5/2013 |
| WO | 2019131333 A1 | 7/2019 |

OTHER PUBLICATIONS

Gosline et al., "The Mechanical Design of Spider Silks: From Fibroin Sequence To Mechanical Function", The Journal of Experimental Biology, 1999, vol. 202, pp. 3295-3303.
International Search Report for Corresponding International Application No. PCT/JP2019/016308 (1 Page) (Aug. 6, 2019).
Supplementary European Search Report for Corresponding European Application No. 19788473.7, Dec. 8, 2021 8 Pages.
Office Action for Corresponding Indian Application No. 202017048890, Mar. 3, 2023, 5 pages.
Reddy et al., "Structure and properties of ultrafine silk fibers produced by Theriodopteryx ephemeraeformis", Journal of Materials Science, 2010, vol. 45, pp. 6617-6622.
Office Action for Corresponding Japanese Patent Application No. 2020-514393, Dec. 13, 2022, 4 pages.

\* cited by examiner

METHOD FOR PRODUCING THREAD BUNDLE OF BAGWORM SILK THREAD

CROSS-REFERENCE TO RELATED APPLICATIONS

This application is a 371 of PCT/JP2019/016308, filed Apr. 16, 2019, which claims the benefit of Japanese Patent Application No. 2018-078522, filed Apr. 16, 2018.

TECHNICAL FIELD

The present invention relates to a method for producing a thread bundle consisting of foothold silk thread derived from moth larva belonging to the family Psychidae, i.e. a bagworm.

BACKGROUND ART

The thread consisting of an insect cocoon or a hair of mammal has been used as an animal fiber for clothes and the like since long ago. Especially, silk thread from a silk moth (*Bombyx mori*) larva, namely a silkworm, which is herein often referred to as "silkworm silk thread", has excellent properties for absorption and desorption of moisture, moisture retention, and heat retention, and also has a unique gloss and a smooth texture. Therefore, the silkworm silk thread is valuable and expensive natural material even today.

However, there exist animal fibers in nature having properties comparable or superior to those of silkworm silk thread. Recently, for utilizing an animal fiber having such excellent properties as novel natural material, exploration thereof and research and development thereon are ongoing.

A thread from a spider (often referred to herein as "spider thread") is one material of interest. A spider thread has flexibility and elasticity and has an elastic force up to 5 to 6 times greater than that of polystyrene, and is thus expected as a medical material for surgical suture, for example, and as a special material for emergency ropes, protective clothes, or the like (Non-Patent Literatures 1 and 2). However, mass-production of spider threads is not feasible because mass rearing of spiders and collecting a large amount of thread from spiders are difficult, which also results in a problem of high production cost. An attempt to solve this problem is ongoing by using gene recombination technology to produce a spider thread in a host such as a silkworm or *Escherichia coli* (Patent Literatures 1 and 2). However, a silkworm or *Escherichia coli* for spider thread production is a recombinant and is thus allowed to be reared or cultured only in facilities with predetermined equipment, which poses a problem of large maintenance or management burden. Additionally, a liquid spider thread protein expressed in *Escherichia coli* needs to be converted to a fiber, which also causes a problem in that the number of processes increases accordingly. Furthermore, another problem is that the current spider thread spun by a recombinant silkworm is merely comprised in silkworm silk thread at several percentages and cannot be obtained as 100% spider thread which allows 100% of the properties of spider thread to be utilized.

There exists an insect called a bagworm (alias "basket worm"). The larvae of moths belonging to the family Psychidae in the order Lepidoptera is collectively referred to as a bagworm and is known to spend the whole larval stages living with a spindle-shaped or cylinder-shaped nest made of pieces of leaves and twigs assembled by thread, as shown in FIG. 1, during which the larva usually hide itself inside the nest and move with the nest even for eating.

The silk thread spun by the bagworm (herein often referred to as "bagworm silk thread") has recently been attracting attention as a new animal-fibrous natural material having more excellent properties than the silkworm silk thread and the spider thread. For example, the bagworm silk thread from the bagworm *Eumeta minuscula* has an elastic modulus up to 3.5 times of that of the silkworm silk thread and up to 2.5 times of that of the *Nephila clavata* spider thread, and a very high strength (Non-Patent Literatures 1 and 2). Additionally, the bagworm silk threads not only have a gloss and a shiny appearance comparable or superior to those of the silkworm silk threads but also allow production of much fine, thin and light fabric with a smooth texture compared to the silkworm silk thread because a monofiber of the bagworm silk thread has a cross-sectional area only about one-seventh of that of the silkworm silk thread.

The bagworm is more advantageous than the silkworm and the spider also in terms of rearing. The bagworm is phytophagous, as is the silkworm. Thus, differently from the spider, which is carnivorous, the bagworm food is easy to procure and can be supplied stably. Additionally, the bagworm is phytophagous similarly to but more advantageously than the silkworm. For example, since the silkworm feeds on only raw leaves of mulberry (species belonging to the genus *Morus*, including, for example, *M. bombycis, M. alba*, and *M. lhou*) in principle, the region for rearing and season for rearing depend on the supply area of mulberry leaves and the season of mulberry leaf development. In contrast, the bagworm is euryphagous, the specificity for food leaves is low, and many species of the bagworm can feed on leaves of trees of various species. Accordingly, food leaves for the bagworm are easily obtainable and the bagworm can be raised in any region. Also, the bagworm of some species can feed on leaves of evergreen trees. Thus, differently from mulberries, which are deciduous trees, it is possible to supply food leaves all year round. Moreover, the bagworm is smaller in size than the silkworm and requires a rearing space equal to or less than that required for rearing the silkworm, which makes mass rearing easy. Thus, the cost for rearing can be reduced.

Also, the bagworm is superior to the silkworm in terms of productivity. For example, the silkworm spins a large amount of threads only during cocooning and all larvae perform cocooning in the same period. Thus, thread collection periods overlap, and labor periods concentrate thereon. However, the bagworms repeatedly spin silk thread for nest building or migration throughout larval stages. Thus, labor periods can be dispersed by artificially adjusting the thread collection periods.

As described above, the bagworm silk thread has properties superior to those of the silkworm silk thread and the spider thread, and also has many advantages for their production, and thus, is expected as a very promising novel natural material.

However, the bagworm silk thread has several problems in the practical application thereof. One of them is a problem associated with the characteristics of the bagworm nest. Contaminants, such as pieces of leaves and twigs, are inevitably attached on the surface of the bagworm nest. This is due to the habit of the bagworm incorporating small pieces of twigs and leaves into the nests from the surroundings for camouflage in the process of nest production and expansion. These contaminants need to be completely removed for commercialization of the bagworm silk thread. In conventional methods, these contaminants are manually removed from the built nest, or are detached after the nest being immersed in warm water for a long time to be softened.

However, the work of removing these contaminants requires enormous labor. Additionally, complete removal of the contaminants is not possible with existing technologies, resulting in a problem in that only low quality final products can be obtained, due to contamination with a small amount of small pieces of leaves and the like, as well as light-brown staining of the bagworm silk thread with pigments from the contaminants and so on. A decolorization treatment can be performed using a base or an acid to remove the pigments, but can result in a marked decrease in quality such as an impaired strength of the bagworm silk thread.

The bagworm silk thread comprises a silk thread called a foothold silk thread, as well as a nest silk thread constituting the nest. As shown in FIG. 1B, this foothold silk thread is a bagworm silk thread spun to be used as a scaffold for preventing the bagworm from falling from a branch or the like when the bagworm migrates. The results of the present inventors' studies have revealed that this foothold silk thread is stronger and has excellent mechanical properties than the nest silk thread. Additionally, the foothold silk thread has no contaminant such as pieces of leaves and twigs, differently from the nest silk thread. Accordingly, if the foothold thread can be collected to be utilized, it can serve as a practical bagworm silk thread.

However, the migration of the bagworm is difficult to control and relies on the insect, which moves among the same places, consequently posing a problem in that the spun silk thread is in multiple crossover and can be obtained only in the form of a complicated entanglement (FIG. 1C). Additionally, the bagworm silk thread is spun in the form of a mixture of a fiber component and a paste-like component covering the surface thereof, and in the case of the foothold silk thread, the paste-like component is attached to the surface of the branch or leaf as a base material, and thus fixes the foothold silk thread to the base material. This fixation by the paste-like component is relatively strong, posing a problem in that, when collected, the foothold silk threads layered on the base material are mechanically peeled and thereby damaged into pieces.

CITATION LIST

Patent Literature

Patent Literature 1: WO2012/165477
Patent Literature 2: WO2013/065651

Non-Patent Literature

Non-Patent Literature 1: Shigeyosi Ohsaki, 2002, Sen'i Gakkaishi (Sen'i To Kogyo), 58: 74-78.
Non-Patent Literature 2: Gosline J. M. et al., 1999, 202, 3295-3303.

SUMMARY OF INVENTION

Technical Problem

A purpose of the present invention is to develop and provide a method of allowing most of the bagworm foothold silk thread spun onto a base material to be collected without damaging the thread. Another purpose is to use the method to allow such a bagworm foothold silk thread for practical application as a novel natural material.

Solution to Problem

To solve the problems described above, the present inventors have vigorously made studies, and as a result, have arrived at the counterintuitive idea of dissolving the base material itself to collect the remaining foothold silk thread, instead of collecting the spun foothold thread by peeling the thread from the base material, and thus, have succeeded in collecting the spun foothold silk thread in the form of a thread bundle in substantially complete condition without causing any physical damage by peeling. The thread bundle consisting of the collected foothold silk thread can be used as an unwoven fabric, and allowing the thread to be spun onto a base material having a desired three-dimensional shape and then collected makes it possible to produce a three-dimensional unwoven fabric that is difficult to process out of a planar material. The present invention provides the following based on the method described above.

(1) A method for producing a thread bundle of a bagworm silk thread, comprising:
placing process of placing a bagworm together with a solvent-soluble base material(s);
spinning process of allowing the bagworm to spin the bagworm silk thread onto the solvent-soluble base material(s);
dissolving process of dissolving the solvent-soluble base material(s) with a solvent; and
separation process of separating the bagworm silk thread spun onto the base material(s) from the solvent-soluble base material(s),
wherein the solvent does not damage, denature, or dissolve the bagworm silk thread.
(2) The method according to (1), further comprising collection process of collecting the bagworm together with a nest after the spinning process and before the dissolving process.
(3) The method according to (1) or (2), wherein the solvent is water.
(4) The method according to (1) or (2), wherein the solvent is a low-polarity solvent.
(5) A method for producing a thread bundle of a bagworm silk thread, comprising:
placing process of placing a bagworm together with a thermally meltable base material(s);
spinning process of allowing the bagworm to spin the bagworm silk thread onto the thermally meltable base material(s);
melting process of melting the thermally meltable base material(s) under heating at a temperature which does not damage, thermally denature, or melt the bagworm silk thread; and
separation process of separating the bagworm silk thread spun onto the base material(s) from the thermally meltable base material(s).
(6) The method according to (5), further comprising collection process of collecting the bagworm together with a nest after the spinning process and before the melting process.
(7) The method according to any one of (1) to (6), further comprising washing process of washing the separated bagworm silk thread.
(8) The method according to any one of (1) to (7), further comprising drying process of drying the separated bagworm silk thread.
(9) The method according to any one of (1) to (8), wherein the base material(s) is/are placed on a support.
(10) The method according to any one of (1) to (9), wherein the base material(s) has/have a planar shape or three-dimensional shape.

(11) An unwoven fabric formed of a bagworm silk thread(s) obtainable by using the method for producing a thread bundle according to any one of (1) to (10).

The present specification encompasses the contents disclosed in the specification and/or drawings of Japanese Patent Application No. 2018-078522, on which the priority of the present application is based.

Advantageous Effects of Invention

By the method for producing a thread bundle according to the present invention, it is possible to allow a bagworm foothold silk thread spun onto a base material(s) to be collected in the form of a thread bundle at a high collection rate without any mechanical damage.

BRIEF DESCRIPTION OF DRAWINGS

FIG. 3a shows a gelatin cast film having a diameter of 9 cm and a thickness of approximately 0.1 mm as a water-soluble base material. FIG. 3b shows the plastic dish fixed to the ice cup with masking tape. A white circle observed in the dashed line circle and a white blur therein in FIG. 3c are foothold silk threads spun by the bagworm. FIG. 3d shows the gelatin cast film peeled from the plastic dish after the foothold silk thread was spun on the plastic dish. FIG. 3e shows the gelatin cast film immersed in boiled water. FIG. 3f shows the foothold silk thread obtained by the method of the present invention.

DESCRIPTION OF EMBODIMENTS

1. Method for Producing Thread Bundle
1-1. Overview

The first aspect of the present invention is a method for producing a thread bundle of a bagworm silk thread. A method for producing according to the present invention is a method in which a bagworm is placed on a solvent-soluble base material(s) or a thermally soluble base material(s), and allowed to spin a foothold silk thread, and then, the base material(s) is/are dissolved or melted to separate the base material component(s) from the spun foothold silk thread in order to collect intended bagworm foothold silk thread and obtain a thread bundle. By the method according to the present invention, it is possible to prevent physical damage by a mechanical operation such as peeling to a foothold silk thread spun onto the base material(s), and to collect the foothold silk thread on the base material(s) efficiently without loss, and produce a thread bundle.

1-2. Definition of Terms

The following terms frequently used herein are defined as described below.

The term "bagworm" collectively refers to a moth larva belonging to the family Psychidae in the order Lepidoptera, as described above. Moths belonging to the family Psychidae are distributed worldwide and the larva (bagworm) of any species of the moth spends the whole larval stages living in a nest covered with natural materials, such as pieces of leaves and twigs, which are assembled by silk threads spun by the larva itself. Furthermore, any species of bagworm has the habit of building a nest using, in principle, base materials in the surroundings when taken out of a nest. Accordingly, the species, instar, and gender of bagworms used herein are not limited, as long as that the bagworm is a larva of a moth species belonging to the family Psychidae and that the species has the habit as described above. For example, the family Psychidae includes the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, etc., and the bagworm used herein may be a species belonging to any genus. Additionally, the instar of the larva may be any instar between the first instar and the last instar. However, larger bagworm is preferable to obtain a large mass of the bagworm silk thread. For example, among larvae of the same species, larva in the last instar is more preferable, and female larva is more preferable than male larva because female grows larger than male. Furthermore, among the family Psychidae, large species is more preferable. For example, *Eumeta japonica* and *Eumeta minuscula*, which are large species, are suitable as species used in the present invention.

Figure 1:
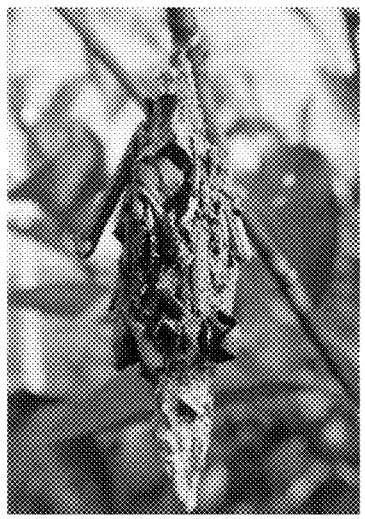
FIG. 1A shows the appearance of a nest of a bagworm of *Eumeta japonica* (*Eumeta japonica* bagworm).
FIG. 1B shows the spinning behavior of a *Eumeta japonica* bagworm in migration. This shows how the bagworm moves while spinning a foothold silk thread (as shown by the arrowhead) and hooks its claws onto the spun foothold silk thread (as shown by the thin arrows).
FIG. 1C shows the state of the bagworm silk thread, which is a foothold silk thread spun onto a plastic plate by the *Eumeta japonica* bagworm. This shows how foothold silk threads spun in a zigzag pattern are entangled complicatedly.
Figure 1:
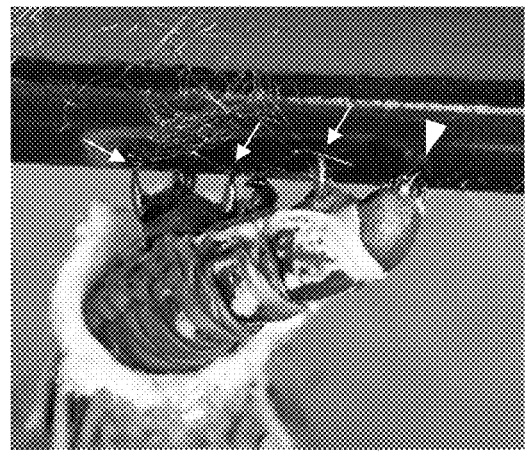
Figure 1:
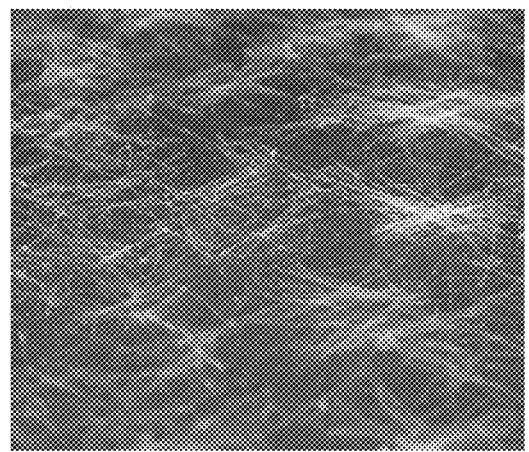

A bagworm to be used in a method for producing according to the present invention is, but is not limited to, a bagworm keeping a nest. "Keeping a nest" refers to the state in which the bagworm has a nest therewith. As described above, the bagworm lives with its own nest, and exposes only part thereof out of the nest even during eating and moving, as shown in FIG. 1B, and in principle, the bagworm never exposes its whole body out of the nest throughout the whole larval stage. When the bagworm is artificially separated from the nest and wholly exposed to the outside, the bagworm thus made naked prioritizes rebuilding a nest for self-protection and to keep itself warm, and thus spins a nest silk thread. Accordingly, it is preferable to allow the bagworm to keep its nest so as to spin a foothold silk thread that is a purpose of the present invention.

The term "silk thread" as used herein refers to a thread derived from an insect and made of proteins, which is spun by the insect in larval or adult stage for the purpose of nest building, migration, anchoring, cocooning, prey capture, and the like. When the term "silk thread" is simply recited herein, it refers to a general silk thread from unspecified insect. In case of indicating a silk thread from a particular insect species, the name of the organism is placed before the term "silk thread," as "silkworm silk threads" or "bagworm silk threads."

The term "bagworm silk thread" as used herein refers to silk threads spun by a bagworm. The "bagworm silk thread" herein encompasses a monofiber, spun fiber, and fiber assembly. The term "monofiber", which is also referred to as monofilament, is the smallest filament unit constituting fiber components. The monofiber contains a fibroin protein as a main component. The bagworm silk thread and the silkworm silk thread in natural states are spun in the form of bifilament in which two monofibers are joined together by a sericin protein, a gummy material. This bifilament is referred to as a "spun fiber". The bagworm nest and the silkworm cocoon are constituted with spun fiber(s). Also, a fiber bundle formed by assembling plural spun fibers is referred to as a "fiber assembly (or multifilament)". Raw silk thread obtained after undergoing a silk reeling process is this multifilament. Furthermore, silk thread obtained by treatment of raw silk thread with an enzyme and a basic chemical such as soap, lye, sodium carbonate, and urea to remove sericin protein is called scoured silk thread.

The bagworm silk thread includes two kinds of the silk thread: a foothold silk thread and a nest silk thread. As described above, the "foothold silk thread" refers to silk thread spun by a bagworm for the purpose of its migration, which has a function as a scaffold for preventing it from falling from branch, leaf, or the like. A bagworm spins the foothold silk thread in the intended direction and in a zigzag pattern upon its migration, and the bagworm hooks its claws onto the foothold silk thread to move. On the other hand, the "nest silk thread" refers to the silk thread forming a nest, which is spun to assemble pieces of leaves and twigs or to make an internal wall of a nest so that its accommodation space becomes a comfortable environment. The bagworm silk thread herein refers to the foothold silk thread unless otherwise specified.

The term "thread bundle" as used herein refers to a silk thread aggregate consisting of a bagworm silk thread(s) alone. A bagworm nest is an aggregate of a bagworm silk thread(s), but commonly is a mixture of contaminants of small pieces of twigs, leaves, and the like, and thus, is not the thread bundle according to the present invention. Accordingly, the thread bundle in the present invention can usually be produced through some artificial process. The state of the thread bundle is not limited. The bagworm silk thread(s) may be in a complicatedly entangled state or in a bundled state in which one or more threads are wound.

The term "base material" as used herein refers to a base for collecting a foothold silk thread. The thread is collected by allowing the bagworm to move on the surface of this base material and to attach the foothold silk thread there. A raw material constituting the base material and the appearance of the base material, such as the shape, will be described below.

The term "solvent" as used herein refers to a solvent that does not damage, denature, or dissolve bagworm silk threads, particularly fibroin protein that is a fiber component of the thread. For example, none of a strong acidic solvent and a strong basic solvent that denature protein is suitable as a solvent to be used in the present invention. The solvents can be classified into high-polarity solvent (hydrophilic solvent) and low-polarity solvent (hydrophobic solvent) based on the degree of their polarity, and both solvents are encompassed herein. High-polarity solvent includes water and some organic solvents, such as lower alcohol (methanol, ethanol, etc.), and acetic acid. Also, low-polarity solvent includes many other organic solvents (low-polarity organic solvent), such as hexane, toluene, chloroform, dichloromethane, dichloroethane, trichloroethylene, acetone, diethyl ether, xylene, carbon tetrachloride, methyl acetate, ethyl acetate, tetrahydrofuran, acetonitrile. Considering the easiness of handling (including waste liquid disposal), safety, and purchasing cost, water (including warm water and hot water) is particularly preferable as a solvent in the present invention.

The term "solvent-soluble" used herein refers to the capability to dissolve in the solvents mentioned above. Accordingly, a "solvent-soluble base material" refers to a base material that can dissolve in a specific solvent.

The term "thermally meltable (or thermally soluble)" as used herein refers to the property that readily melts by heat. The term "thermally meltable base material" refers to a base material that is solid state at normal temperature (15° C. to 25° C.) under atmospheric pressure and melts and becomes liquid state by heat. The melting point of a thermally meltable base material may be any temperature, as long as the temperature is lower than a temperature which causes the bagworm silk thread to be damaged, thermally denatured, or melted. The bagworm silk threads start thermally decomposing over 260° C., and thus, the melting point may be 260° C. or less at the highest. The melting point is preferably 200° C. or less, more preferably 150° C. or less, 140° C. or less, 130° C. or less, or 120° C. or less. To reduce the heating cost and not to expose the bagworm silk thread to high temperature more than necessary, the melting point is preferably a temperature which is higher than normal temperature and is 100° C. or less. For example, a suitable range is from 40° C. to 100° C., from 45° C. to 98° C., from 50° C. to 95° C., from 55° C. to 90° C., from 60° C. to 85° C., from 65° C. to 80° C., or from 70° C. to 75° C.

2. Producing Method

Figure 2A:
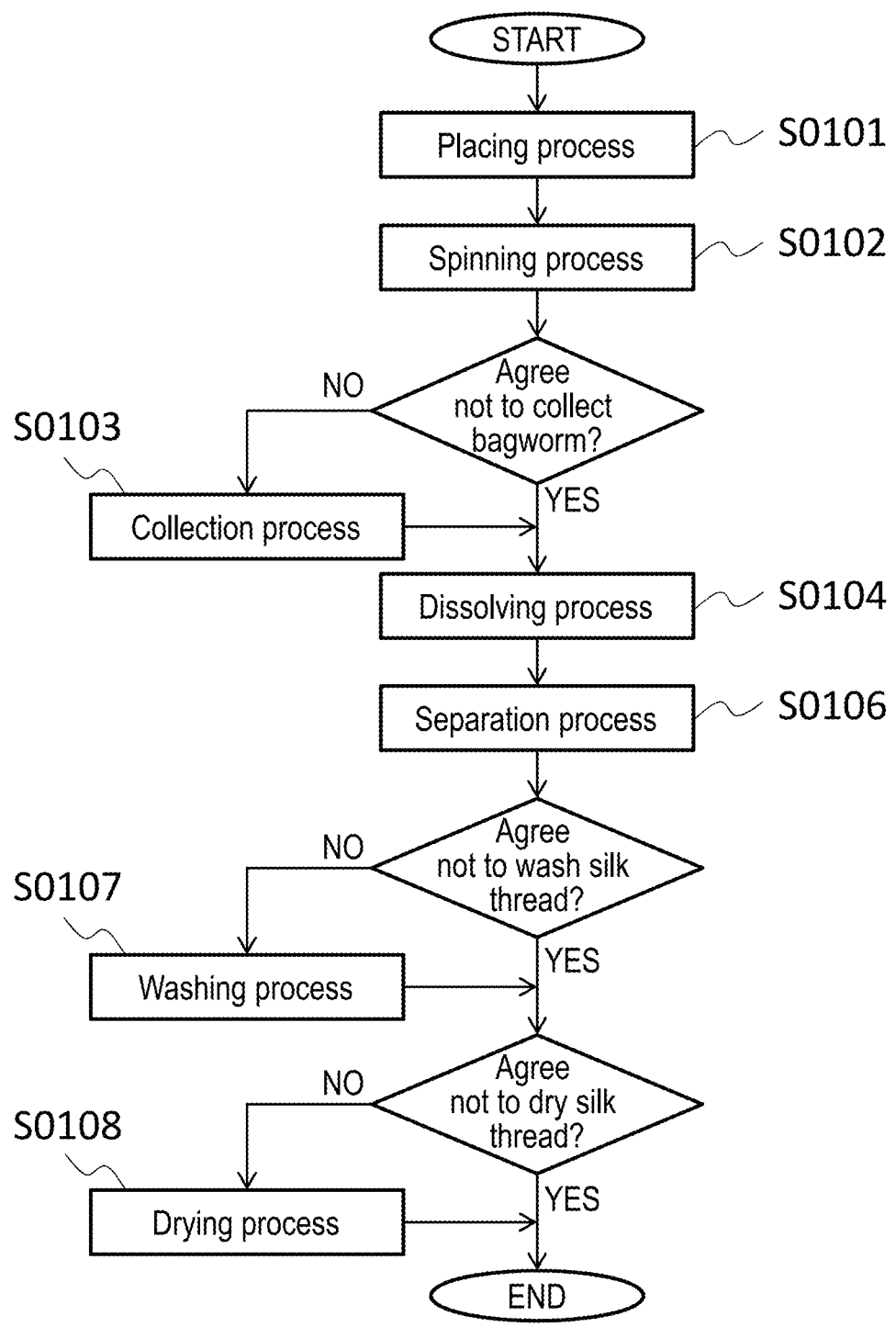
FIG. 2A shows a process flow diagram of a method for producing a bagworm silk thread according to the present invention. This flow diagram shows a case in which the base material to be used is a solvent-soluble substance.
Figure 2B:
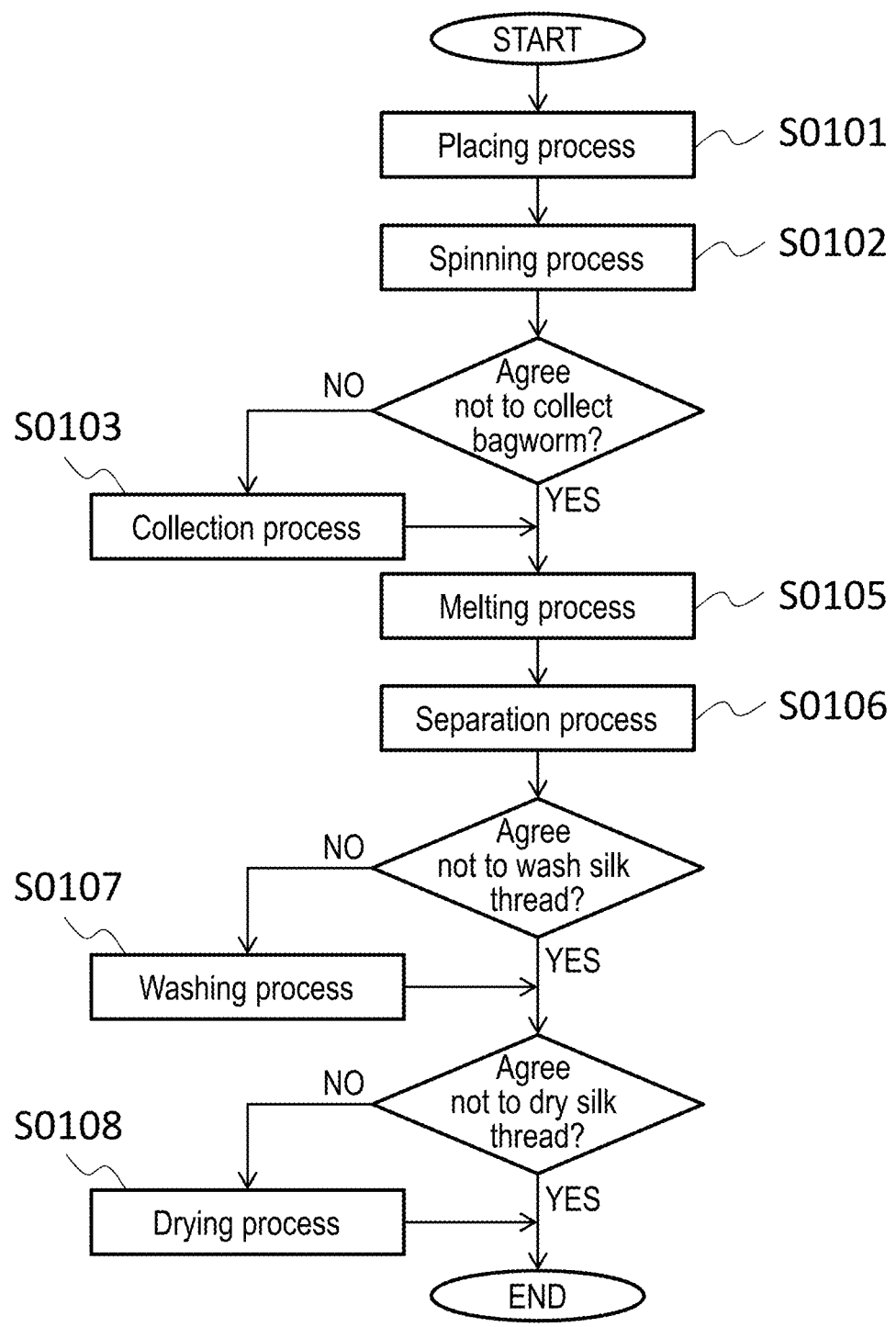
FIG. 2B shows a process flow diagram of a method for producing a bagworm silk thread according to the present invention. This flow diagram shows a case in which the base material to be used is a thermally meltable substance.

The process flow diagram of this aspect is shown in FIG. 2A and FIG. 2B. As shown in these figures, a method for producing threads according to the present aspect is consisting of two independent flows: the first flow (FIG. 2A) and the second flow (FIG. 2B).

2-1. Pre-Treatment

Pre-treatment of a bagworm used in a method according to the present invention will be described here.

In the present method, live bagworm is used in a placing process and a spinning process in both the first flow and the second flow. However, the bagworm is not fed, in principle, during these processes. In the present invention, the longer the migration distance of the bagworm per unit time is, the more foothold silk thread can be obtained. However, if the bagworm is fed during thread collection, it is possible that the bagworm is carried away with eating and hardly moves. In a sense, spinning a thread involves discharging a protein (bagworm silk thread) synthesized and accumulated in the body, meaning that the bagworm consumes a large amount of energy and protein when migrating. Thus, it is preferable that the bagworm subjected to a method for producing according to the present invention is sufficiently fed beforehand in the pre-treatment. The method and time for feeding are not limited. The bagworm may be supplied with a sufficient amount of food until they stop eating.

In addition, it is preferable to allow the bagworm to defecate after it is fed. This is for preventing the foothold silk thread spun by the bagworm from getting dirty with feces.

Leaving the bagworm at a usual rearing temperature for sufficient time for defecation after completion of feeding is enough for the defecation treatment. For example, the bagworm may be left at a temperature of 10 to 30° C., preferably 15 to 25° C. for, 30 minutes or more, 1 hour or more, 2 hours or more, 3 hours or more, 4 hours or more, 6 hours or more, 8 hours or more, 24 hours or less, 20 hours or less, 18 hours or less, 15 hours or less, 12 hours or less, or 10 hours or less.

2-2. First Flow

The first flow (FIG. 2A) is characterized in that a solvent-soluble substance is used as a base material. The present flow comprises a placing process (S0101), spinning process (S0102), dissolving process (S0104), and separation process (S0106) as essential processes and further comprises a collection process (S0103), washing process (S0107), and drying process (S0108) as optional processes. Each of the processes will be described below.

2-2-1. Placing Process

The "placing process" (S0101) is a process of placing a bagworm together with a solvent-soluble base material. This process is an essential process in the present invention.

A solvent-soluble base material used in this process is not limited as long as the material is soluble in the solvent described above. Here, such a base material is classified into water-soluble base material (water-soluble material) and low-polarity solvent-soluble base material, and is specifically described below.

The term "water-soluble base material" as used herein means a base material consisting of a substance that is soluble in water and is solid state under a dry environment. "Under a dry environment" refers to an environment under a normal state (at 15° C. to 25° C. under an atmospheric pressure condition) and humidity of 50% or less, preferably 40% or less, 30% or less, 20% or less, or 10% or less. Specific example of water-soluble base material comprises gelatin, starch, pullulan, and the like. A water-soluble base material used in this process may be, but not limited to, one base material or a combination of two or more base materials selected from the group mentioned above. The water-soluble base material may be soluble not only in water (pure water) but also in an aqueous solution containing one solute or two or more solutes.

The term "low-polarity solvent-soluble base material" as used herein means a base material consisting of a substance that is soluble in a low-polarity solvent and is solid state under the normal state described above. A "low-polarity solvent" as used herein corresponds mainly to a low-polarity organic solvent. Specific example thereof comprises hexane, toluene, chloroform, dichloromethane, dichloroethane, trichloroethylene, benzene, acetone, diethyl ether, xylene, methyl acetate, ethyl acetate, carbon tetrachloride, acetonitrile, and the like. For example, low-polarity solvent-soluble base material comprises, but not limited to, polystyrene, vinyl acetate, cellulose acetate, acrylic resin, and polycarbonate. The material may be a combination of two or more low-polarity solvent-soluble base materials as long as they are soluble in the same solvent.

The thickness of a solvent-soluble base material used in this process is not limited. In cases where the base material is made too thick, the base material itself can obtain rigidity, but adversely, not only the production cost of the base material increases, but also the base material is difficult to dissolve in the dissolving process, and to be separated from the base material in the separation process. In addition, in cases where the base material is made too thin, the production cost of the base material can be controlled, and the dissolution of the base material in the dissolving process and the separation of the base material from the foothold silk thread in the separation process are easier, but adversely, the base material itself loses rigidity, failing to retain a given shape and to carry out a function as a base. Accordingly, the thickness can suitably be determined taking into account the production cost and rigidity of the base material, the easiness of processing in the subsequent processes, and the like. In the case of the water-soluble base material, the base material usually, but without limitation, has an average thickness of preferably 0.5 mm or more, 0.6 mm or more, 0.7 mm or more, 0.8 mm or more, 0.9 mm or more, 1.0 mm or more, 1.2 mm or more, or 1.5 mm or more, and in addition, preferably 3.0 mm or less, 2.8 mm or less, 2.5 mm or less, 2.2 mm or less, or 2.0 mm or less. In cases where the water-soluble base material is consisting of a thin film having an average thickness of less than 0.5 mm, 0.4 mm, 0.3 mm, 0.2 mm, or 0.5 mm, the base material itself does not have enough rigidity to retain a given shape, and thus, the base material may be placed on a suitable support having a desired shape.

The term "support" as used herein refers to a member on the surface of which the solvent-soluble base material is placed so that rigidity and/or a shape is given to the solvent-soluble base material. The support is an optional constituent to be used in the method for producing according to the present invention, and can be used if necessary.

The material of the support is not particularly limited, provided that it has enough rigidity to retain a given shape. Examples thereof comprise glass, metal, plastic, synthetic rubber, ceramic, or paper, a piece of plant (comprising, for example, a piece of wood), or a piece of animal (comprising, for example, a piece of bone, seashell, and sponge). The thermally soluble base material described below can also be used for a support. Besides, a solvent-soluble base material which is different in its properties from a solvent-soluble base material to be used as a spinning base can be used for a support. Examples thereof comprise a case in which a thin film of the water-soluble base material is used as a solvent-soluble base material for spinning and in which a low-polarity-solvent-soluble base material with the water-soluble base material being attached to the surface is used as a support.

The shape and size of a base material used in this process are not limited. For example, the shape may be a sheet-like or plate-like planar shape, or may be a three-dimensional shape. Obtaining a planar unwoven fabric consisting of a bagworm foothold silk thread can be achieved by using a planar base material to allow the bagworm to spin a thread onto the whole planar portion thereof. Additionally, obtaining an unwoven fabric that is consisting of a foothold silk thread and has a desired three-dimensional shape can be achieved by using a base material having the desired three-dimensional shape to allow the bagworm to spin a thread onto the whole surface of the base material. Such an unwoven fabric having a three-dimensional shape can be used, for example, as a scaffold material in regenerative therapy.

The size of the base material can be that which is selected as necessary, and in view of the fact that the foothold silk thread is a bagworm silk thread spun during migration, the lower limit is preferably, but is not limited to, a size equal to or greater than the size of the bagworm and the body length of the bagworm. For example, the long axis or the major axis can be 1 cm or more, 2 cm or more, 3 cm or more, 4 cm or more, or 5 cm or more. On the other hand, the size of the base material is not limited to any upper limit, but in cases where the long axis or the major axis is 10 cm or more, 15 cm or more, 20 cm or more, 25 cm or more, or 30 cm or more, it is more preferable to allow a plurality of bagworms to spin threads.

"Placing a bagworm together with a solvent-soluble base material" refers to positioning both of them such that the bagworm can touch the surface of the solvent-soluble base material. For example, the bagworm may be directly placed on the base material, or be placed so that the bagworm can migrate to reach the base material. Specific examples of the latter option comprise a case in which a bagworm is placed on the bottom of a lidless wide-mouthed plastic container, and then, a solvent-soluble base material is used as a lid for the container. The bagworm prefers a higher position and accordingly migrates along the inner sidewall of the wide-mouthed plastic container to reach the undersurface of the base material corresponding to the ceiling of the container, followed by spinning a foothold silk thread while moving on the base material.

In this regard, the species and the number of the bagworm to be placed are not limited. For example, one bagworm or a plurality of bagworms may be placed at one time per base material onto which the foothold silk thread is to be spun. Additionally, the species and the age of the bagworm to be placed are not limited. In cases where a plurality of bagworms is placed, the individuals may be of the same species and the same age, or may be a mixture of bagworms of different species or different ages.

2-2-2. Spinning Process

The "spinning process" (S0102) is a process of allowing a bagworm to move to the surface of the base material and spin a foothold silk thread thereon. This process is an essential process in the present invention.

The period of this process varies depending on the species and age of the bagworm and the number of individuals to be used, and is not to be limited. The spinning may be continued until the required amount of foothold silk thread onto the base material is reached. For example, when one last instar bagworm of *Eumeta japonica* is used to spin a thread onto a circular base material having a diameter of 9 cm, the bagworm is allowed to spin for 1 day or more, 2 days or more, 3 days or more, 4 days or more, 5 days or more, 6 days or more, or 7 days or more. As described above, the foothold silk thread is spun while the bagworm moves, and thus, the obtained foothold silk thread is in proportion to the migration distance of the bagworm on the base material. Therefore, by using a plurality of bagworms to spin, time of the spinning process is shorter than that by using a single bagworm to spin. In addition, the bagworm is not allowed to eat food while spinning, and thus, the bagworm often stops spinning in this process. In such a case, the bagworm may be exchanged for a new one to continuously maintain the spinning process.

It is recommended that the changes of temperature and humidity in the present process be none or little so that the amount of thread spun by a bagworm per unit time can be larger. It is preferable that the temperature is around 20° C., for example, ranges from 15° C. to 25° C., or from 18° C. to 22° C., and that the humidity is around 50%, for example, ranges from 40% to 65%, or from 45% to 60%. There is no limit about light and dark period during this process, and it may have only a light period, or may have cyclical light and dark periods. For example, the cycle may be such that, in 24 hours, the light period is 6 hours to 18 hours, 7 hours to 17 hours, 8 hours to 16 hours, 9 hours to 15 hours, 10 hours to 14 hours, 11 hours to 13 hours, or 12 hours, and the rest is the dark period.

2-2-3. Collection Process

The "collection process" (S0103) is a process of collecting the bagworm used in the spinning process together with the nest, and is an optional process in the present invention. A purpose of this process is to separate the bagworm no longer required from the base material and collect it.

After the spinning process, the spun foothold silk thread and the bagworm which has spun the thread coexist on the base material. However, the bagworm is not needed in the subsequent dissolving process. In addition, the bagworm that has stopped spinning is no longer required even in the period of the spinning process. Furthermore, when the bagworm together with the base material and the foothold silk thread is treated with a solvent in the dissolving process, it is possible that the bagworm silk thread is stained with an undesirable color by the bodily fluid of the bagworm and a extract of dead leaves and the like used for the nest, that the nest silk thread coexists, or that the bagworm and the nest decrease dissolution efficiency of the base material. Thus, although the present process is an optional process, the collection before the dissolving process is preferable.

The method for collecting a bagworm from the base material is not limited. Any method for separating a bagworm from the base material can be utilized. For example, the bagworm in contact with the base material may be peeled away together with the nest. However, for purposes of the present invention, it is preferred that the damage to the foothold silk thread is as low as possible. For example, the bagworm may be induced to spontaneously leave the base material. Specific examples of such a method comprise a method in which, utilizing the feature of the bagworm, which moves to a higher place, the container is turned upside down so that the position of the base material can be changed from the ceiling to the bottom. After the bagworm moves to the inner sidewall of the container, the base material can be collected. Another method is heating of the base material. The bagworm spontaneously leaves the base material to escape from high temperature, and thus, the base material can be collected after the migration. The heating temperature may be ordinary temperature or more and the temperature without the damage of the bagworm silk thread and melting the base material. For example, the temperature may be 30° C. or more, 33° C. or more, 35° C. or more, 38° C. or more, 40° C. or more, 42° C. or more, 45° C. or more, 48° C. or more, or 50° C. or more, and 80° C. or less, 75° C. or less, 70° C. or less, 65° C. or less, 60° C. or less, or 55° C. or less.

Incidentally, the collected bagworm can be fed and then reused in the method for producing according to the present invention.

2-2-4. Dissolving Process

The "dissolving process" (S0104) is a process of dissolving a solvent-soluble base material with a solvent. It is an essential process in the present invention. In this process, a solvent-soluble base material in a solid state is dissolved to turn into a liquid state.

A solvent to be used in this process is a solvent which can dissolve the solvent-soluble base material used in the spinning process. For example, if a water-soluble base material is used in the spinning process, the solvent is water (pure water) or an aqueous solution containing one solute or two or more solutes. Alternatively, if a low-polarity solvent-soluble base material is used in the spinning process, the solvent is a low-polarity solvent which can dissolve the base material. For a specific example, if the low-polarity solvent-soluble base material is polystyrene or acrylic resin, various kinds of low-polarity solvents such as hexane, xylene, chloroform, and carbon tetrachloride can be used as a solvent.

The temperature of a solvent used in this process is not particularly limited, as long as the temperature does not damage, denature, or dissolve the bagworm silk threads and is the boiling point of the solvent or lower. The temperature is usually in the range of room temperature, for example, from 1° C. to 35° C., from 5° C. to 32° C., from 10° C. to 30° C., from 12° C. to 27° C., from 15° C. to 25° C., or from 18° C. to 20° C. In general, however, a solute often dissolves more easily at a higher solvent temperature. In particular, a water-soluble base material dissolves in a shorter time at a higher water temperature. Thus, the solvent temperature is preferably higher to dissolve the base material rapidly. For example, if the solvent is water, the water temperature under the atmospheric pressure is preferably 35° C. or more, 38° C. or more, 40° C. or more, 42° C. or more, 45° C. or more, 48° C. or more, 50° C. or more, 52° C. or more, 55° C. or more, 58° C. or more, 60° C. or more, 62° C. or more, 65° C. or more, 68° C. or more, 70° C. or more, 72° C. or more, 75° C. or more, 78° C. or more, 80° C. or more, 82° C. or more, 85° C. or more, 88° C. or more, 90° C. or more, 92° C. or more, 95° C. or more, or 98° C. or more. Incidentally, the solvent can be heated before and/or during this process.

The method for dissolving a base material is not limited, as long as the solvent-soluble base material can contact with the solvent. For example, the method comprises a method for immersing a solvent-soluble base material into a solvent, and a method for spraying or splashing a solvent-soluble base material with a solvent. The spun foothold silk thread may contact with the solvent. In cases where the solvent-soluble base material is immersed in a solvent, the solvent may be stirred with, for example, a stirring bar or a stirring rod to enhance the dissolution efficiency.

The dissolving time is a time until after the solvent-soluble base material is completely dissolved in the solvent. A specific time can be determined as appropriate based on the property of the base material and the type, temperature, and amount of the solvent. For example, if the base material is polystyrene and is immersed and treated in a xylene or carbon tetrachloride solvent, at normal temperature, the lower limit may be 5 seconds or more, 10 seconds or more, 15 seconds or more, 20 seconds or more, 25 seconds or more, 30 seconds or more, 45 seconds or more, 50 seconds or more, or 60 seconds or more. Additionally, the upper limit may be 10 minutes or less, 8 minutes or less, 5 minutes or less, 3 minutes or less, or 2 minutes or less.

2-2-5. Separation Process

The "separation process" (S0106) is a process of separating a dissolved solvent-soluble base material and foothold silk threads. It is an essential process in the present invention. The method for separating bagworm silk threads and a solvent containing a dissolved base material after the dissolving process is not limited. The foothold silk thread is a fibrous solid, but a solvent containing a base material is liquid, and thus, an existing method for separating solid and liquid can be utilized. For example, the separation can be performed by centrifugation using a dehydrating device and the like. The bagworm itself, the nest, and sometimes its feces remain as the solid if the collection process described above has not been performed. In this case, for example, it is not limited, but the foothold silk thread can simultaneously be separated from not only the solvent, but also the bagworm and the like by entwining the foothold silk thread around a rod and the like.

After this process, the intended bagworm foothold silk thread can be obtained.

2-2-6. Washing Process

The "washing process" (S0107) is a process of washing the separated foothold silk threads. This process is an optional process and may be performed if necessary. In order to obtain a purer foothold silk thread without solvent-soluble base material contamination, it is preferable to select the present process.

In some cases, the foothold silk thread obtained from the separation process has the remaining solvent containing the dissolved solvent-soluble base materials. In such a case, it is possible that the dissolved solvent-soluble base materials are polymerized again when the solvent is evaporated. Therefore, it is preferable that the solvent is completely removed by wash. By this process, part of the feces or the like attached to the foothold silk thread can be removed simultaneously.

A washing solution used for wash in this process may be a solvent used in the dissolving process. If a low-polarity solvent was used in the dissolving process, another solvent having high compatibility with the low-polarity solvent can be used as a washing solution. A washing solution having high volatility is preferable. In one example, if xylene is used as a solvent in the dissolving process, another low-polarity solvent such as toluene, benzene, or a polarity solvent such as ethanol can be used as a washing solution. In this regard, a solvent containing no other component is preferable as a washing solution. If a water-soluble base material is used, for example, pure water (including warm water) is more preferable as a washing solution than an aqueous solution containing any other solute.

The washing method is not limited, as long as the solvent used in the dissolving process can be removed from the foothold silk threads. The foothold silk threads may be sprayed with the washing solution or immersed in the washing solution. After the wash, the washing solution attached to the foothold silk threads can be removed in the same manner as in the separation process.

The number of washes is not limited. The wash can be performed once or plural times. The term "plural times" as used herein refers to, for example, 2 to 20 times, 2 to 15 times, 2 to 10 times, 2 to 7 times, 2 to 5 times, 2 to 4 times, or 2 to 3 times. In general, the wash is preferably performed plural times. If the wash is performed plural times, the washing solution to be used at each time may be the same or different. Also, the washing methods may be the same or different.

2-2-7. Drying Process

The "drying process" (S0108) is a process of drying the collected foothold silk thread. It is an optional process to be performed, if necessary, in the present invention. On the foothold silk thread obtained from the separation process or the washing process, some solvent or washing solution remains. This process is a process to remove the solvent or washing solution remaining on the foothold silk thread after the separation process or the washing process by drying. After this process, the intended foothold silk thread can be obtained.

The drying method is not particularly limited, as long as the amount of the remaining solvent or washing solution can be reduced without denaturing or deteriorating the foothold silk thread. For example, the method comprises a natural drying method (including sun drying) in which it is exposed to external air to vaporize the solvent or washing solution, an air drying method in which a blowing device or the like is used to blow them with warm air or cold air, a dehumidification drying method in which a dehumidifying agent is placed together in a hermetically sealed space for a given period of time, a heat drying method in which the solvent or washing solution is evaporated and dried by heating, a decompression drying method in which evaporation is performed by degasification with a vacuum pump or the like in a container, or combinations thereof.

The drying time may be suitably determined depending on the solvent or washing solution used, the drying method used, and the like. For example, if a volatile solvent or washing solution such as xylene or ethanol is used and it is dried with an air drying method, drying time with 5 seconds to 10 minutes, 10 seconds to 5 minutes, or 20 seconds to 3 minutes is enough.

2-3. Second Flow

The second flow (FIG. 2B) is characterized in that a thermally meltable substance is used as a base material. The present flow comprises a placing process (S0101), spinning process (S0102), melting process (S0105), and separation process (S0106) as essential processes and further comprises a collection process (S0103), washing process (S0107), and drying process (S0108) as optional processes. Each of the processes will be described below.

2-3-1. Placing Process

The placing process (S0101) in the second flow is an essential process, and is basically the same as the placing process in the first flow. Accordingly, only the different points from the placing process in the first flow will be described below.

This process is different from the placing process in the first flow in that a thermally meltable base material is used instead of a solvent-soluble base material as a base material.

The thermally meltable base material is not limited to any kind. Any raw material having the characteristics of the thermally soluble base material described in the above-mentioned definition can be used. Specific examples of a thermally meltable base material that can be used in the second flow comprise wax. The wax comprises plant-based waxes such as Japan wax and animal-based wax such as beeswax. The shape and size of the thermally meltable base material are in accordance with that of the solvent-soluble base material in the first flow.

2-3-2. Spinning Process

The "spinning process" (S0102) in the second flow is an essential process, and is the same as the spinning process in the first flow except that a thermally meltable base material is used as a base material. Accordingly, this process may be performed in accordance with the spinning process in the first flow.

2-3-3. Collection Process

The "collection process" (S0103) in the second flow is an essential process, and is basically not different from the collection process in the first flow. Accordingly, this process may be performed in accordance with the collection process in the first flow.

2-3-4. Melting Process

The "melting process" (S0105) is an essential process characteristic of the second flow, and is a process of melting a thermally soluble base material by heating. In this process, a base material in a solid state turns into a liquid state by melt.

The heating temperature for melting the thermally soluble base material in this process is not particularly limited, as long as temperature is higher than the melting point of the thermally meltable base material and does not damage, denature, or melt the bagworm silk thread. Since the melting point which is the lower limit of the heating temperature differs depending on the thermally meltable base material, it may be determined appropriately according to the thermally meltable base material used. Furthermore, since the bagworm silk thread do not thermally decompose at 260° C. or less, as described above, the upper limit of the heating temperature may be any temperature of 260° C. or less. However, the possibility of damage or denature by heat cannot be eliminated if the bagworm silk thread exposed to a high temperature over 200° C. for a long time. Therefore, the upper limit of the heating temperature is preferably the melting point of the thermally meltable base material used+50° C. or less, the melting point+45° C. or less, the melting point+40° C. or less, the melting point+35° C. or less, the melting point+30° C. or less, the melting point+25° C. or less, the melting point+20° C. or less, the melting point+15° C. or less, the melting point+10° C. or less, or the melting point+5° C. or less.

The method for melting a base material is not particularly limited, as long as the method can heat the thermally soluble base material. For example, the method comprises a method in which the thermally soluble base material is placed on and heated with a heater or a hot plate, a method in which the thermally meltable base material is placed in and heated with a microwave oven (a microwave), a method in which the thermally meltable base material is exposed to hot air, a method in which the thermally meltable base material is melted in a hot water bath in cases where the melting point of the thermally meltable base material is lower than 100° C., and the like.

The melting time is a time until after the thermally soluble base materials are completely melted. A specific time can be appropriately determined based on the property of the thermally soluble base material and the heating temperature. For example, if the base material is beeswax having a melting point of 62° C., the melting time may be 30 minutes, 40 minutes, 50 minutes, 60 minutes, 70 minutes, 80 minutes, or 90 minutes under the heating temperature of 80° C.

2-3-5. Separation Process

The "separation process" (S0106) is an essential process, and is a process of separating the foothold silk threads and the liquified thermally meltable base material. The separation process in the second flow basically has the same procedures as the separation process in the first flow. In the first flow, the foothold silk thread and the solvent containing the dissolved solvent-soluble base material are separated. However, this process in the second flow is different in that a liquified thermally meltable base material is separated. The foothold silk thread is a fibrous solid, but the thermally meltable base material in this process is in liquid state through the melting process, and thus, an existing method for separating solid from liquid can be utilized in accordance with the separation process in the first flow. However, if the temperature in this process becomes lower than the melting point of the thermally meltable base material, the thermally meltable base material starts being polymerized back to be solidified. Therefore, the thermally meltable base material should be prevented from being polymerized back before and in this process. For example, heating may be continued in this process at the comparable temperature as in the melting process, a polymerization inhibitor or a polymerization retarder may be supplied, or a diluent to be used in the washing process described below may be added in this process so that a liquid mixture of the thermally meltable base material and the diluent can be formed and then separated.

2-3-6. Washing Process

The "washing process" (S0107) is an optional process, and is a process of washing the separated foothold silk threads. The washing process in the second flow basically has the same procedure as the washing process in the first flow. However, the second flow is different from the first flow in that the melted thermally meltable base material is attached to the separated foothold silk thread. Accordingly, only the points in which the flows are different will be specifically described here.

In this process, if the temperature becomes lower than the melting point of the thermally meltable base material, the attached base material is polymerized back to be solidified. Thus, the thermally meltable base material is desirably removed completely by washing.

A washing solution used for wash is not particularly limited, as long as a solvent does not damage, denature, or dissolve the foothold silk threads, and has a temperature higher than the melting point of the thermally meltable base material used. For example, if the thermally meltable base material is a beeswax having a melting point of 62° C., the beeswax attached to the foothold silk thread can be melted and removed using water at 70° C. or more as a washing solution. A more preferable washing solution is a diluent having high compatibility with the thermally meltable base material. In this case, the temperature of the diluent is not necessarily higher than the melting point of the thermally meltable base material. The term "diluent" as used herein refers to a solvent in which the melted thermally meltable base material can easily be dissolved. For example, using beeswax as a thermally meltable base material, a diluent can be a solvent such as chloroform, carbon tetrachloride, and xylene.

2-3-7. Drying Process

The "drying process" (S0108) in the second flow is an optional process, and is the same as the drying process in the first flow. Accordingly, this process may be performed in accordance with the drying process in the first flow.

2-4. Effect

Conventional technology has a problem in that it is difficult that the bagworm foothold silk thread spun onto the base material is collected without mechanical damage to the thread.

By the method for collecting a thread and the method for producing a thread bundle according to the present invention, it is possible that, instead of peeling and collecting the foothold silk thread spun onto the base material by the bagworm, the base material itself is dissolved or melted to separate the liquified base material and the fibrous bagworm silk thread so that the above-mentioned problems can be solved, resulting in stably obtaining a thread bundle only consisting of a bagworm foothold silk thread and having excellent mechanical characteristics.

3. Unwoven Fabric Constituted with Foothold Silk Thread 3-1. Overview

The second aspect of the present invention is an unwoven fabric constituted with a foothold silk thread of a bagworm silk thread. An unwoven fabric according to the present invention is constituted with a thread bundle obtained using the method for producing according to the first aspect.

3-2. Constitution

The thread of a thread bundle obtained by the method for producing according to the first aspect presents a reticular form because the bagworm spins with migrating on the base material. When spun so as to form a multilayer, the thread is already in the form of an unwoven fabric on the base material. Accordingly, the thread bundle consisting of the bagworm foothold silk thread obtained by the method for producing according to the first aspect can itself be utilized as an unwoven fabric.

Additionally, in cases where, in the method for producing according to the first aspect, when the foothold silk thread is layered on the whole surface of the base material made in three-dimensional shape, the thread bundle can become an unwoven fabric having a shape tracing to the three-dimensional shape of the base material. By using the base material with a desired three-dimensional shape, it is possible to use the foothold silk thread, for example, as a scaffold material for a cultured cell in regenerative therapy and as a natural unwoven fabric having no influence on a human body.

Furthermore, the thread bundle obtained by the method for producing according to the first aspect can be made into an unwoven fabric by an existing method for producing an unwoven fabric. Without limitation, a spun lace method or a needle-punching method can be utilized as an existing method for producing an unwoven fabric.

Examples

<Method for Producing Thread Bundle of Bagworm Silk Thread Using Water-soluble Base Material>

(Purpose)

A method according to the present invention is used to produce a thread bundle constituted with a bagworm foothold silk thread.

(Method and Result)

As a bagworm, a last instar larva of *Eumeta japonica* (*Eumeta japonica* bagworm) was used. As a base material, gelatin, which is a water-soluble base material among solvent-soluble base materials, was used.

(1) Production of Gelatin Cast Film

Figure 3:
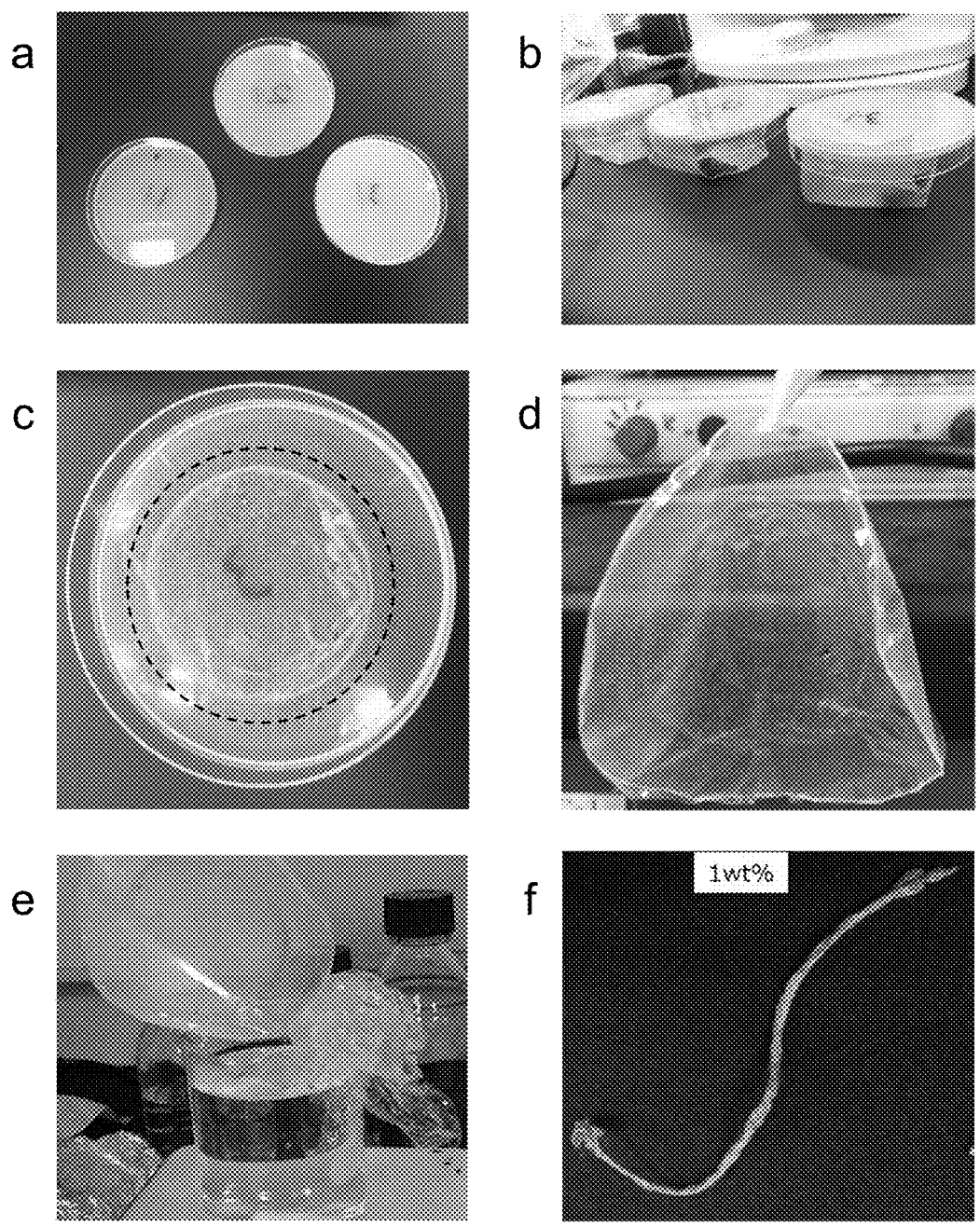
FIG. 3 explains an Example of the present invention.

Gelatin used for a medical capsule is easily dissolved in water at 40° C. or more. Owing to this, a gelatin capsule was used to produce a gelatin cast film as a base material onto which a foothold silk thread was to be spun. A suitable amount of city water was provided in a beaker, and heated using a hot stirrer until the water boiled. After the boiling, a gelatin capsule (manufactured by Capsugel Japan Inc.) was dissolved in the water at a concentration of 1 wt %. After the dissolution, the solution was placed in 9-cm plastic dishes in an amount (10 mL) enough to spread over the whole bottom face of the dish, and dried at room temperature. This yielded a gelatin cast film having a diameter of 9 cm and a thickness of approximately 0.1 mm as a water-soluble base material (FIG. 3*a*). The plastic dishes themselves were used as supports for the base material.

(2) Placing Bagworm and Spinning

Ice cups (manufactured by Mineron Kasei Co., Ltd.) were used as containers for spinning. The bagworms of *Eumeta japonica*, one each per container, were placed in ice cups, and then, the gelatin cast film produced with the water-soluble base material in (1) described above, together with the plastic dish as a support, was placed as the lid on the ice cup with the gelatin cast film facing downward. Then, the plastic dish was fixed to the ice cup with masking tape (FIG. 3*b*). Subsequently, the bagworm was allowed to spin, without being fed, at a temperature of 25° C. under the condition of a light to dark ratio of 16:8 for five days. However, the first placed bagworm stopped in spinning on Day 2, and thus, collected and replaced with a new last instar bagworm of *Eumeta japonica*.

(3) Collection and Dissolution of Gelatin Cast Film

After the spinning, the gelatin cast film and the plastic dish were separated from the ice cup. At this point of time, the surface of the gelatin cast film had innumerable foothold silk threads spun thereon (FIG. 3*c*). Subsequently, the gelatin cast film was peeled from the plastic dish (FIG. 3*d*), and immersed in boiled water with stirring for five minutes (FIG. 3*e*). The gelatin cast film was completely dissolved in the boiled water, and then, the foothold silk thread floating on the boiled water was collected. Then, the collected foothold silk thread was washed with fresh boiled water, and dried at room temperature. As a result, the foothold silk thread shown in FIG. 3*f* was obtained. The surface of the collected foothold silk thread was observed under a stereoscopic microscope, and found to be free from a gelatin residue. The results described above have revealed that, by the method for producing a thread bundle of a bagworm silk thread according to the present invention, it is possible to obtain a thread bundle consisting of a pure foothold thread alone.

All publications, patents, and patent applications cited herein should be incorporated herein by reference in their entirety.

The invention claimed is:

1. A method for producing a thread bundle of a bagworm foothold silk thread, comprising:
   placing process of placing a bagworm together with a solvent-soluble base material(s);
   spinning process of allowing the bagworm to spin the bagworm foothold silk thread onto the solvent-soluble base material(s);
   dissolving process of dissolving the solvent-soluble base material(s) with a solvent; and
   separation process of separating the bagworm foothold silk thread spun onto the base material(s) from the solvent-soluble base material(s), and
   wherein the solvent does not damage, denature, or dissolve the bagworm foothold silk thread.

2. The method according to claim 1, further comprising collection process of collecting the bagworm together with a nest after the spinning process and before the dissolving process.

3. The method according to claim 1, wherein the solvent is water.

4. The method according to claim 1, wherein the solvent is a low-polarity solvent.

5. The method according to claim 1, further comprising washing process of washing the separated bagworm foothold silk thread.

6. The method according to claim 1, further comprising drying process of drying the separated bagworm foothold silk thread.

7. The method according to claim 1, wherein the base material(s) is/are placed on a support.

8. The method according to claim 1, wherein the base material(s) has/have a planar shape or three-dimensional shape.

9. An unwoven fabric formed of a bagworm foothold silk thread(s) obtainable by using the method for producing a thread bundle according to claim 1.

10. A method for producing a thread bundle of a bagworm foothold silk thread, comprising:
    placing process of placing a bagworm together with a thermally meltable base material(s);
    spinning process of allowing the bagworm to spin the bagworm foothold silk thread onto the thermally meltable base material(s);
    melting process of melting the thermally meltable base material(s) under heating at a temperature which does not damage, thermally denature, or melt the bagworm foothold silk thread; and
    separation process of separating the bagworm foothold silk thread spun onto the base material(s) from the thermally meltable base material(s).

11. The method according to claim 10, further comprising collection process of collecting the bagworm together with a nest after the spinning process and before the melting process.

* * * * *